(12) United States Patent
Tao

(10) Patent No.: US 11,779,236 B2
(45) Date of Patent: Oct. 10, 2023

(54) VASCULAR ASSESSMENT DEVICE

(71) Applicant: CardiacM CO., Ltd., Zhunan Township, Miaoli County (TW)

(72) Inventor: Teh-Ho Tao, Zhunan Township (TW)

(73) Assignee: FINEDAR BIOMEDICAL TECHNOLOGY CO. LTD., Hsinchu (TW)

( * ) Notice: Subject to any disclaimer, the term of this patent is extended or adjusted under 35 U.S.C. 154(b) by 549 days.

(21) Appl. No.: 16/998,407

(22) Filed: Aug. 20, 2020

(65) Prior Publication Data

US 2021/0275049 A1    Sep. 9, 2021

(30) Foreign Application Priority Data

Mar. 5, 2020    (TW) .................................. 109107218

(51) Int. Cl.
*A61B 5/05*      (2021.01)
*A61B 5/00*      (2006.01)
(Continued)

(52) U.S. Cl.
CPC .............. *A61B 5/05* (2013.01); *A61B 5/6801* (2013.01); *C08L 33/04* (2013.01); *C08L 79/08* (2013.01);
(Continued)

(58) Field of Classification Search
CPC ............ H01Q 1/38; H01Q 1/40; H01Q 1/526; H01Q 9/0407; H01Q 9/40; H01Q 1/273;
(Continued)

(56) References Cited

U.S. PATENT DOCUMENTS

| | | | | |
|---|---|---|---|---|
| 6,177,909 B1* | 1/2001 | Reid | .................... | H01Q 19/062 343/792.5 |
| 2016/0143557 A1* | 5/2016 | Kahlman | ............. | A61B 5/6898 600/407 |

(Continued)

FOREIGN PATENT DOCUMENTS

| | | |
|---|---|---|
| CN | 105796177 A | 7/2016 |
| CN | 107072553 A | 8/2017 |

(Continued)

OTHER PUBLICATIONS

Mukai et al., "Relationships between structure and microwave dielectric properties in cotton fabrics", Materials Research Express, 7, published Jan. 6, 2020 (Year: 2020).*

(Continued)

*Primary Examiner* — Eric F Winakur
*Assistant Examiner* — Jonathan Drew Moroneso
(74) *Attorney, Agent, or Firm* — Birch, Stewart, Kolasch & Birch, LLP

(57) ABSTRACT

A vascular assessment device includes an antenna unit and a fabric unit. The antenna unit includes a substrate, a transmitting antenna and a receiving antenna spaced apart disposed on the substrate, and a circuit module disposed on the substrate. The circuit module cooperates with the transmitting antenna to emit a carrier radio wave toward a fistula of a subject, and receives, via the receiving antenna, a return wave signal formed through reflection of the carrier radio (Continued)

wave. The fabric unit is sleeved on the antenna unit, and includes an isolating layer adapted to be disposed between the transmitting antenna and the skin above the fistula. The fabric unit has a dielectric constant not greater than 3.

13 Claims, 7 Drawing Sheets

(51) Int. Cl.
| | | |
|---|---|---|
| *C08L 79/08* | (2006.01) | |
| *C08L 33/04* | (2006.01) | |
| *H01Q 9/06* | (2006.01) | |
| *D02G 3/04* | (2006.01) | |
| *H01Q 9/04* | (2006.01) | |
| *A61B 5/026* | (2006.01) | |

(52) U.S. Cl.
CPC ........... *D02G 3/045* (2013.01); *H01Q 9/0485* (2013.01); *H01Q 9/06* (2013.01); *A61B 5/026* (2013.01); *A61B 2562/164* (2013.01); *A61B 2562/166* (2013.01); *A61B 2562/182* (2013.01)

(58) Field of Classification Search
CPC ........ H01Q 9/0485; H01Q 9/06; H01Q 23/00; H01Q 1/085; H01Q 3/01; H04Q 9/00; H04Q 2209/40; A61B 5/05; A61B 5/6801; A61B 5/026; A61B 2562/164; A61B 2562/166; A61B 2562/182; A61B 5/25; A61B 5/363; A61B 5/369; A61B 5/6804; A61B 5/721; A61B 5/7264; C08L 33/04; C08L 79/08; D02G 3/045
See application file for complete search history.

(56) References Cited

U.S. PATENT DOCUMENTS

2019/0104982 A1\* 4/2019 Dunn .................... A61B 5/0531
2019/0298208 A1\* 10/2019 Weinstein .......... A61B 5/02438

FOREIGN PATENT DOCUMENTS

| TW | 201800088 A | 1/2016 |
| TW | 201622639 A | 7/2016 |
| TW | 201927176 A | 7/2019 |

OTHER PUBLICATIONS

"Polyimide PCB Material Information (FR4 vs. Polyimide PCB)", Millennium Circuits Limited, published Jul. 19, 2017, published at https://www.mclpcb.com/blog/polyimide-pcb-material-information-fr4-vs-polyamide-pcb/ (Year: 2017).\*
"Fabric Thickness and Weight", Proper Cloth, snapshot of http://propercloth.com/reference/fabric-thickness-weight/ taken from 07/Dec. 2018 via the Wayback Machine https://web.archive.org/web/20180712065647/http://propercloth.com/reference/fabric-thickness-weight/ (Year: 2018).\*
Taiwanese Office Action for application No. 109107218 dated Jul. 14, 2020.

\* cited by examiner

VASCULAR ASSESSMENT DEVICE

CROSS-REFERENCE TO RELATED APPLICATION

This application claims priority of Taiwanese Invention Patent Application No. 109107218, filed on Mar. 5, 2020.

FIELD

The disclosure relates to an antenna device, and more particularly to a vascular assessment device.

BACKGROUND

Patients with chronic renal failure should first undergo arteriovenous fistula surgery before kidney dialysis. Since blood flow of arteriovenous fistula is closely related to the effect of kidney dialysis, an embolic occlusion of arteriovenous fistula may cause poor effect or hinder the procedures of kidney dialysis, resulting in such patients requiring emergency treatment or even hospitalization. Therefore, in order to ensure a good effect of kidney dialysis, it is important to monitor blood flow of arteriovenous fistula in such patients.

Referring to FIG. 1, a conventional system for determining blood flow in a fistula 14 of a patient includes an antenna device, which includes a circuit board 11, and an antenna 12 disposed on the circuit board 11. The antenna 12 is adapted to be in direct contact with a patient's skin 13, and is configured to emit a carrier radio wave toward the fistula 14, and then to receive a return wave signal that is formed through reflection of the carrier radio wave by the fistula 14, which is used to determine blood flow in the fistula 14. However, the emitted carrier radio wave may be reflected off the skin surface and returned directly to the receiving antenna without transmitting through the skin and the subcutaneous tissue to the fistula 14, thereby affecting signal quality and detection accuracy. Therefore, there is still a need to develop a vascular assessment device with improved detection accuracy.

SUMMARY

Therefore, an object of the disclosure is to provide a vascular assessment device that can alleviate or eliminate at least one of the drawbacks of the prior art.

According to the disclosure, the vascular assessment device includes an antenna unit and a fabric unit.

The antenna unit includes a substrate, an antenna module which includes a transmitting antenna and a receiving antenna that are spaced apart disposed on the substrate, and a circuit module which is disposed on the substrate. The circuit module is configured to cooperate with the transmitting antenna to emit a carrier radio wave toward a fistula of a subject, and to receive, via the receiving antenna, a return wave signal which is formed through reflection of the carrier radio wave by the fistula.

The fabric unit is sleeved on the antenna unit, and includes an isolating layer that is adapted to be disposed between the antenna module and the skin above the fistula of the subject. The fabric unit has a dielectric constant that is not greater than 3.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
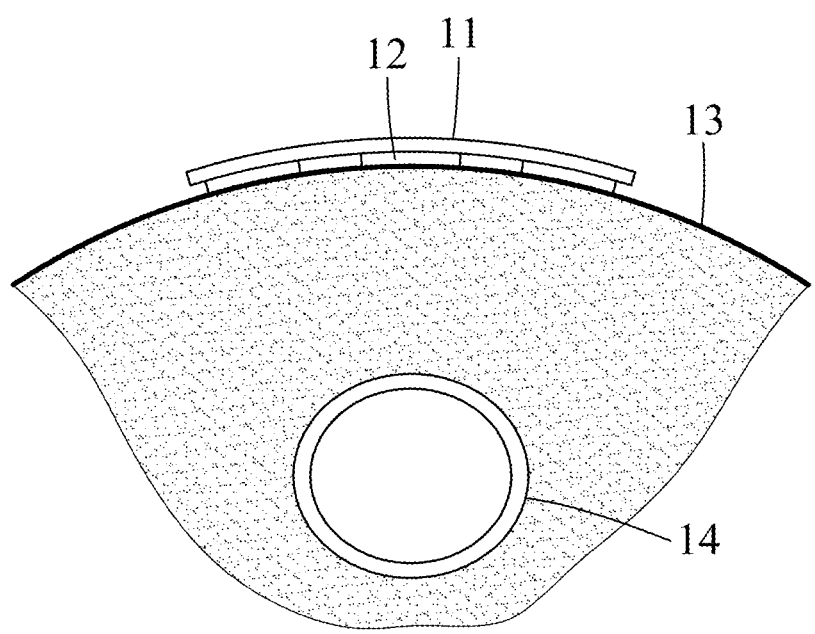
FIG. 1 is a schematic view illustrating a conventional system for determining blood flow in a fistula of a patient.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
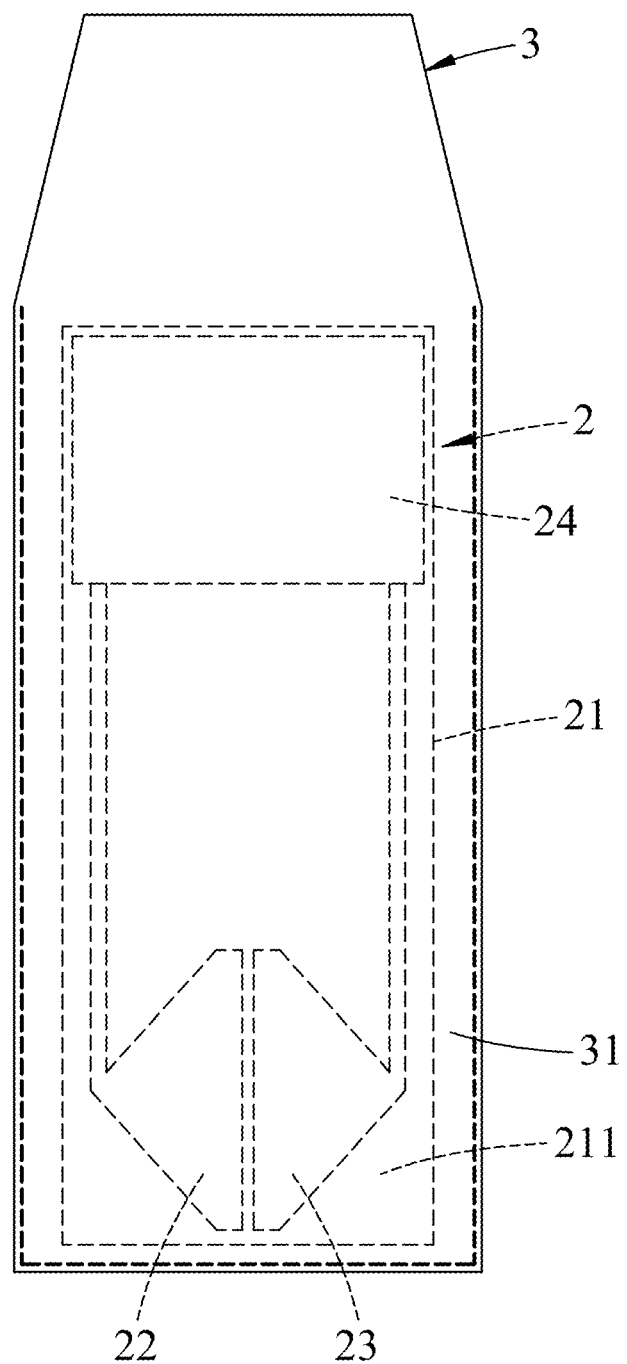
FIGS. 2 and 3 are schematic views respectively illustrating two opposite sides of an embodiment of an vascular assessment device according to this disclosure.
Figure 3:
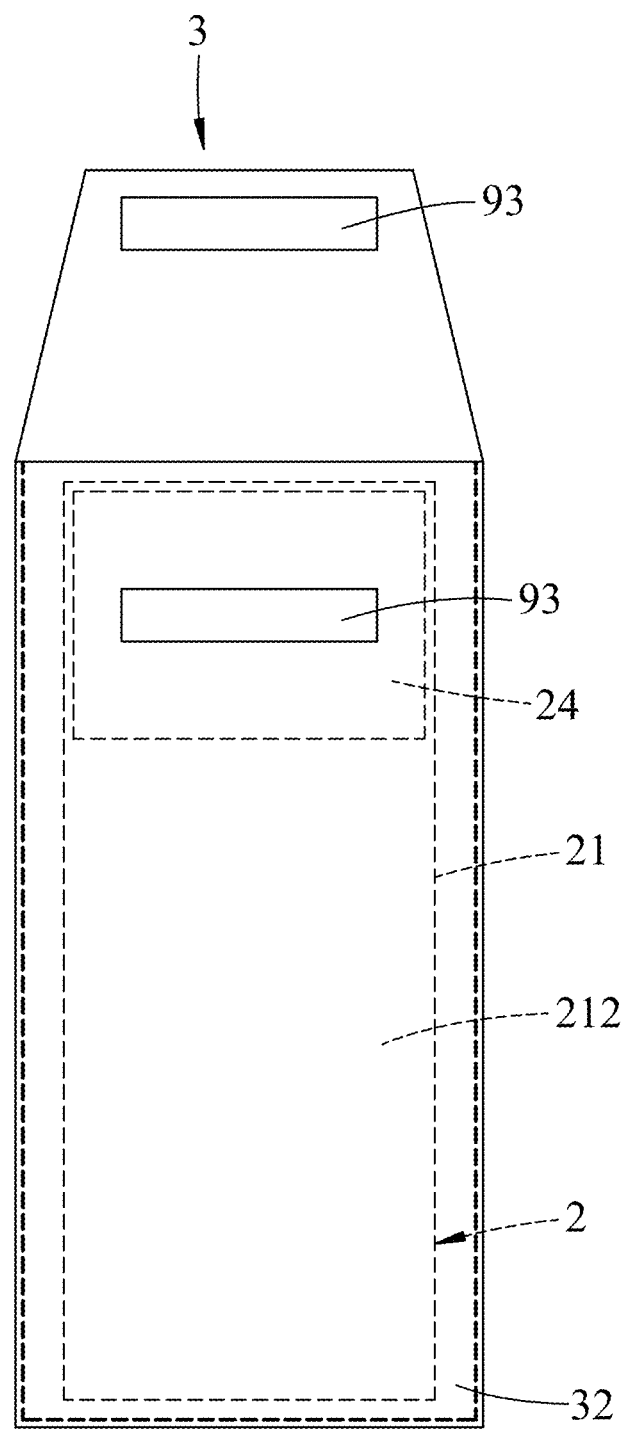
Figure 4:
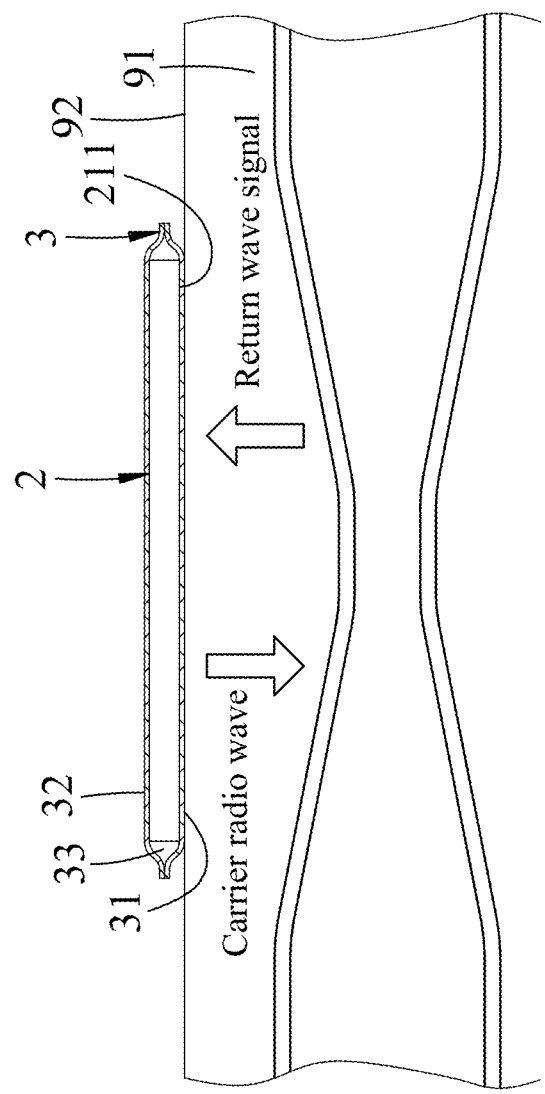
FIG. 4 is a schematic view illustrating the embodiment of the vascular assessment device for determining blood flow in a fistula of a subject.

Referring to FIGS. 2 to 4, an embodiment of a vascular assessment device according to the present disclosure is adapted for use in determining blood flow in a fistula 91 of a subject 9 (e.g., a human patient). The fistula 91 may be present in a blood vessel, which includes, but is not limited to, a brachial artery, a radial artery, or combinations thereof. The vascular assessment device includes an antenna unit 2 and a fabric unit 3.

Figure 5:
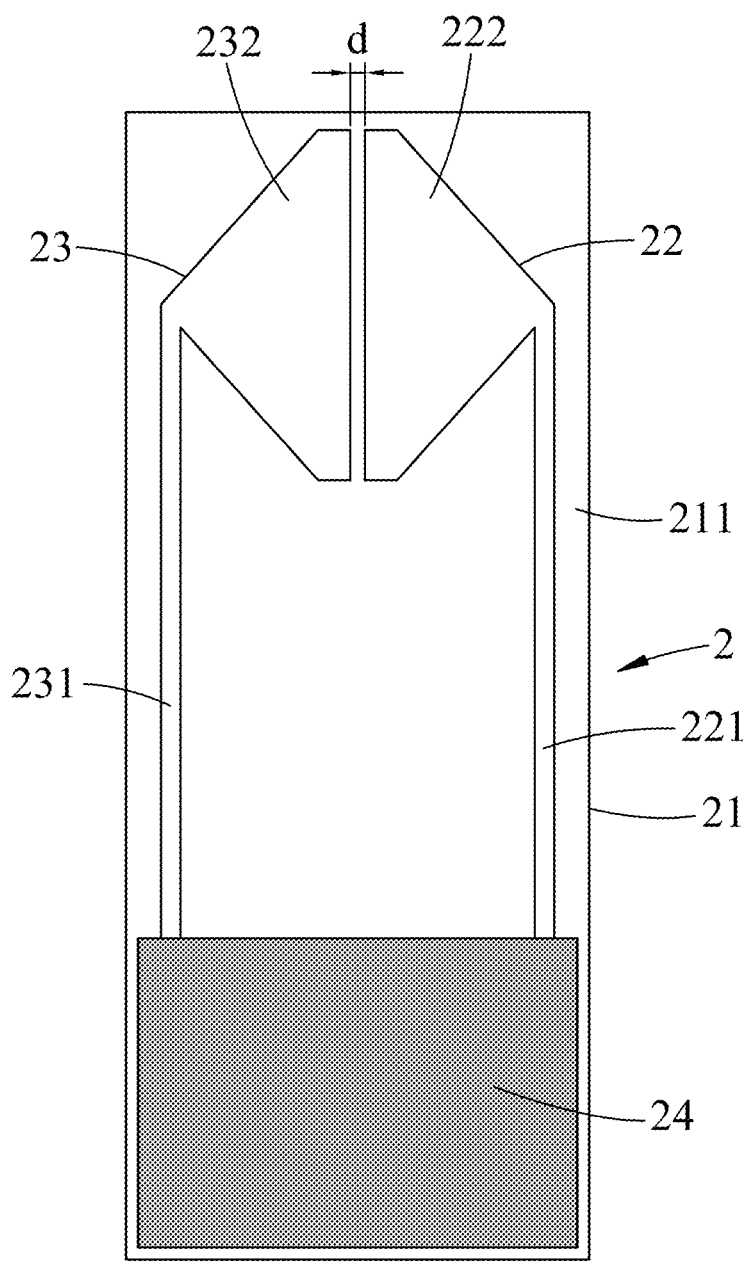
FIGS. 5 and 6 are schematic views respectively illustrating two opposite sides of an antenna unit of the embodiment.
Figure 6:
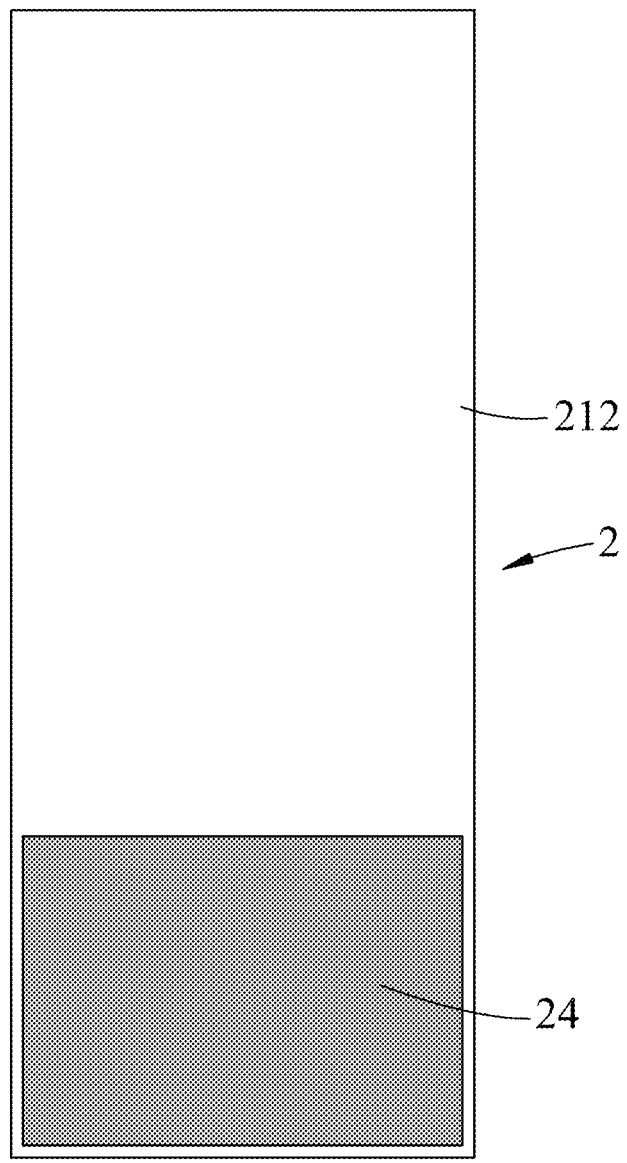

Referring to FIGS. 5 and 6, the antenna unit 2 includes a substrate 21, an antenna module which includes a transmitting antenna 22 and a receiving antenna 23, and a circuit module 24.

The substrate 21 includes a first surface 211 and a second surface 212 that is opposite to the first surface 211. The substrate 21 may be a flexible printed circuit (FPC), which may be made of one of polyimide (PI), and polyester (PET). The substrate 21 may have a thickness that is not smaller than 0.3 mm. In certain embodiments, the substrate 21 may have a thickness of 0.5 mm.

The transmitting antenna 22 and the receiving antenna 23 are spaced apart disposed on the first surface 211 of the substrate 21. The transmitting antenna 22 includes a transmitting component 222 and a transmitting line 221 that extends from the transmitting component 222 to the circuit module 24. The receiving antenna 23 includes a receiving component 232 and a receiving line 231 that extends from the receiving component 232 to the circuit module 24. Each of the transmitting line 221 and the receiving line 231 may have an extending length ranging from 2 cm to 4 cm. The transmitting component 222 and the receiving component 232 are spaced apart from each other by a spacing (d), which may be greater than 0.8 mm.

The transmitting antenna 22 may be a wide band patch antenna. Each of the transmitting component 222 and the receiving component 232 may be in a triangular form. In this embodiment, the transmitting antenna 22 and the receiving antenna 23 are modified half bow-tie antennas.

The circuit module 24 is disposed on the first surface 211 of substrate 21, and is configured to cooperate with the transmitting antenna 22 to emit a carrier radio wave toward the fistula 91, and to receive, via the receiving antenna 23, a return wave signal which is formed through reflection of the carrier radio wave by the fistula 91. Since the configuration of the circuit module 24 for emitting and receiving signal is well known to those skilled in the art, the detail descriptions thereof are not provided herein for sake of brevity.

It should be noted that the frequency bandwidth of the antenna unit 2 may be determined by several factors, such as the thickness of the substrate 21, the extending length of the transmitting line 221 and the receiving line 231, the spacing between the transmitting component 222 and the receiving component 232, etc.

For example, the frequency bandwidth of the antenna unit 2 increases with the increasing thickness of the substrate 21. When the substrate 21 made of a flexible material (e.g., FPC) has a thickness of 0.3 mm, the antenna unit 2 has a frequency bandwidth of around 100 MHz at a simulated return loss (S11) that is less than −10 dB. When the substrate 21 made of a flexible material (e.g., FPC) has a thickness of 0.5 mm, the antenna unit 2 has a frequency bandwidth of greater than 200 MHz at a simulated S11 that is less than −10 dB. When the substrate 21 made of a flexible material has a thickness that is greater than 1.0 mm, the antenna unit 2 has a frequency bandwidth of greater than 1.0 GHz at a simulated S11 that is less than −10 dB. In addition, in other simulation results, when each of the transmitting line 221 and the receiving line 231 has an extending length ranging from 2 cm to 4 cm, the antenna unit 2 has a frequency bandwidth ranging from 0.7 GHz to 1.23 GHz at a simulated S11 that is less than −10 dB. When the spacing between the transmitting component 222 and the receiving component 232 is 0.8 mm, the antenna unit 2 has a frequency bandwidth of 0.7 GHz at a simulated S11 that is less than −10 dB, and the greater the spacing (such as greater than 0.8 mm), the wider the frequency bandwidth of the antenna unit 2. In consideration of the optimized antenna unit 2 to be made, in certain embodiments, the substrate 21 has a thickness of 0.5 mm, and each of the transmitting line 221 and the receiving line 231 has an extending length ranging from 2 cm to 4 cm, and a spacing (d) therebetween is set to be 0.8 mm.

Figure 7:
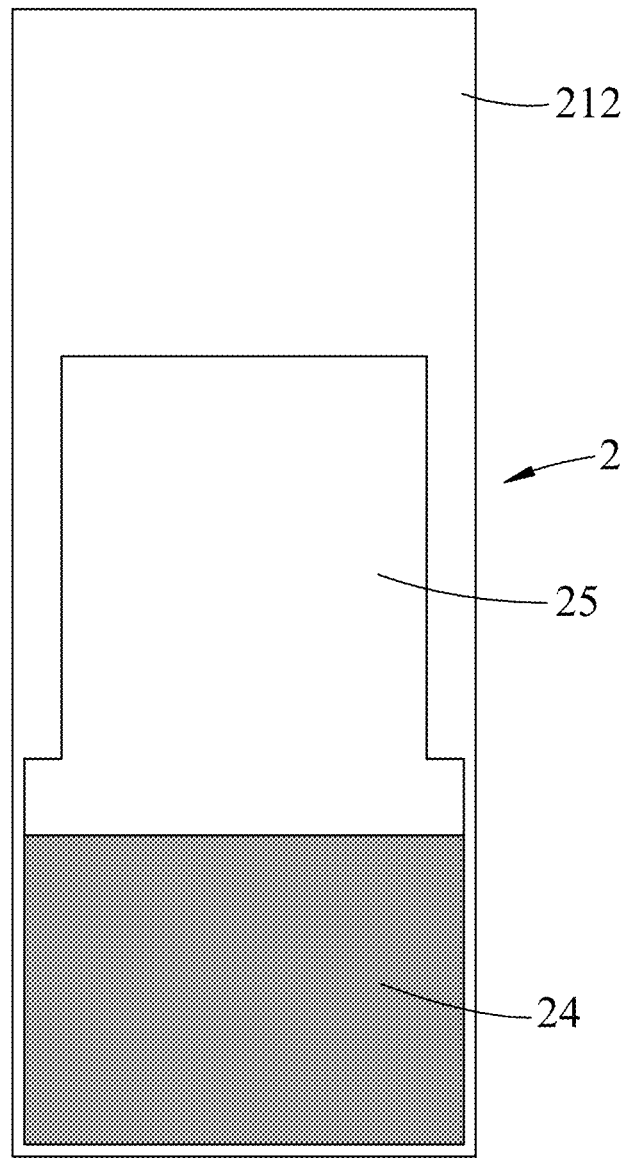
FIG. 7 is a schematic view illustrating the antenna unit in a variation of the embodiment.

Referring to FIG. 7, in a variation of the embodiment, the substrate 21 is made of a non-flexible material (e.g., FR4 glass epoxy material), and the antenna unit 2 may further include a metal shield layer 25 which is disposed on the second surface 212 of the substrate 7. In the simulation result of this variation, the antenna unit 2 may have a frequency bandwidth ranging from 30 MHz to 1 GHz at a simulated S11 that is less than −10 dB.

Referring back to FIGS. 2 to 4, the fabric unit 3 is sleeved on the antenna unit 2, and includes an isolating layer 31 that is adapted to be disposed between the antenna module and the skin 92 above the fistula 91 of the patient, and that has a dielectric constant not greater than 3. The fabric unit 3 may further include a protecting layer 32 (i.e., the other piece of fabric) that cooperates with the isolating layer 31 to form an accommodating space 33 for receiving the antenna unit 2. That is, the antenna unit 2 is separated from the patient's skin 92 by the isolating layer 31, instead of directly contacting the patient's skin 92.

The isolating layer 31 may be a plain weave. In certain embodiments, the isolating layer 31 is made of a Tetoron™ cotton blended fabric. Based on the total weight of the Tetoron™ cotton blended fabric, Tetoron™ may be present in an amount ranging from 30 wt % to 40 wt %, and cotton may be present in an amount ranging from 60 wt % to 70 wt %. In certain embodiments, Tetoron™ is present in an amount of 35 wt % and cotton is present in an amount of 65 wt %. In other embodiments, the isolating layer 31 is made of a flax cotton blended fabric (e.g., a cotton in warp and flax in weft fabric). Based on the total weight of the flax cotton blended fabric, flax is present in an amount of 55 wt %, and cotton is present in an amount of 45 wt %. The average thickness of the flax cotton blended fabric is 0.22 mm and the dielectric constant thereof is 1.97. The isolating layer 31 may have a thickness ranging from 0.2 mm to 0.4 mm.

There are no particular limitations on the shape of each of the isolating layer 31 and the protecting layer 32 and the joining method thereof, and can be varied according to practical requirements. In this embodiment, each of the isolating layer 31 and the protecting layer 32 is in a rectangular shape. The isolating layer 31 is slightly longer than the protecting layer 32, and the isolating layer 31 and the protecting layer 32 are sewed to each other along the peripheries thereof (the sutures are shown as bold dashed lines in FIGS. 2 and 3), so as to form the accommodating space 33. The isolating layer 31 has a protruding end which may be folded back to be releasably joinable to the protecting layer 32 using a fastener, such as hook and loop fasteners 93 used in this embodiment, or zippers, ties, buttons, buckles, or the like. By virtue of the isolating layer 31 joining to the protecting layer 32, the antenna unit 2 can be securely received in the fabric unit 3, making the transmitting antenna 22 and the receiving antenna 23 fully fitting on the skin 92 of the subject 9.

In summary, the vascular assessment device of this disclosure has the following advantages.

Firstly, by virtue of the fabric unit 3 being sleeved on the antenna unit 2, which includes the isolating layer 31 that is adapted to be disposed between the antenna module and the skin 92 above the fistula 91 of the subject 9, and that has a dielectric constant that is not greater than 3 and has a thickness between 0.2 mm and 0.4 mm, which provide optimum conditions for transmitting carrier radio wave to the fistula 14 without signal loss due to reflection at the interface of skin and the transmitting antenna 22. For the same reason, the return wave signal which is formed through reflection of the carrier radio wave by the fistula 91 can be received by the receiving antenna 23, so as to enhance the signal quality, thereby improving the detection accuracy of the vascular assessment device.

Secondly, the fabric unit 3 can protect the antenna unit 2 from damage that may be caused by, e.g. skin oil and perspiration, and can be easily removed after use for further cleaning.

Finally, by adjusting the material and the thickness of the substrate 21 or the isolating layer 31, and/or by adjusting the extending length of the transmitting line 221 and the receiving line 231, or the spacing (d) between the transmitting component 222 and the receiving component 232, the quality of the return wave signal may be further improved, so as to enhance the detection accuracy of the vascular assessment device.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A vascular assessment device adapted for determining blood flow in a fistula of a subject, comprising:
    an antenna unit including
        a substrate,
        an antenna module which includes a transmitting antenna and a receiving antenna that are spaced apart disposed on said substrate, said transmitting antenna being a patch antenna, and
        a circuit module which is disposed on said substrate, and which is configured to cooperate with said transmitting antenna to emit a carrier radio wave toward the fistula, and to receive, via said receiving antenna, a return wave signal which is formed through reflection of the carrier radio wave by the fistula; and
    a fabric unit which is sleeved on said antenna unit, and which includes an isolating layer that is adapted to be disposed between said antenna module and the skin above the fistula of the subject, and that has a dielectric constant that is not greater than 3,
    wherein
    said transmitting antenna is a modified half bow-tie antenna, and includes a transmitting component in a triangular form and a transmitting line that extends from said transmitting component to said circuit module,
    said receiving antenna is a modified half bow-tie antenna, and includes a receiving component in a triangular form and a receiving line that extends from said receiving component to said circuit module,
    each of said transmitting component and said receiving component include a base, and said base of said transmitting component and said base of said receiving component face each other and are spaced apart from each other, and
    each of said transmitting line and said receiving line has an extending length ranging from 2 cm to 4 cm.

2. The vascular assessment device of claim 1, wherein said isolating layer is a plain weave.

3. The vascular assessment device of claim 2, wherein said isolating layer is made of a polyester cotton blended fabric.

4. The vascular assessment device of claim 3, wherein polyester is present in an amount that ranges from 30 wt % to 40 wt %, and cotton is present in an amount that ranges from 60 wt % to 70 wt % based on the total weight of the polyester cotton blended fabric.

5. The vascular assessment device of claim 2, wherein said isolating layer is made of a flax cotton blended fabric.

6. The vascular assessment device of claim 5, wherein flax is present in an amount of 55 wt %, and cotton is present in an amount of 45 wt % based on the total weight of the flax cotton blended fabric.

7. The vascular assessment device of claim 1, wherein said isolating layer has a thickness ranging from 0.2 mm to 0.4 mm.

8. The vascular assessment device of claim 1, wherein said substrate has a thickness that is not smaller than 0.3 mm.

9. The vascular assessment device of claim 1, wherein said substrate is made of a material selected from the group consisting of polyimide, and polyester.

10. The vascular assessment device of claim 1, wherein said fabric unit further includes a protecting layer that is configured to cooperate with said isolating layer to form an accommodating space for receiving said antenna unit.

11. The vascular assessment device of claim 1, wherein said transmitting component and said receiving component are spaced apart from each other by a fixed spacing.

12. The vascular assessment device of claim 11, wherein said spacing is greater than 0.8 mm.

13. The vascular assessment device of claim 1, wherein said antenna unit further includes a metal shield layer disposed on said substrate that is opposite to said transmitting antenna and said receiving antenna.

* * * * *